United States Patent [19]

Elmqvist et al.

[11] Patent Number: 4,790,318

[45] Date of Patent: Dec. 13, 1988

[54] CARDIAC PACER FOR PACING A HUMAN HEART

[75] Inventors: Hakan Elmqvist; Anders Lekholm, both of Bromma; Sven-Erik Hedberg, Mungsängen; David C. Amundson, Bromma, all of Sweden

[73] Assignee: Siemens Aktiengesellschaft, Berlin and Munich, Fed. Rep. of Germany

[21] Appl. No.: 874,597

[22] Filed: Jun. 16, 1986

[51] Int. Cl.[4] .............................................. A61N 1/36
[52] U.S. Cl. .............................. 128/419 PG; 128/723
[58] Field of Search ................ 128/696, 419 PG, 713, 128/419 PT, 723

[56] References Cited

U.S. PATENT DOCUMENTS

| 3,593,718 | 2/1976 | Krasner et al. | 128/419 P |
| 4,303,075 | 12/1981 | Heilman et al. | 128/419 PG |
| 4,337,776 | 7/1982 | Daly et al. | 128/419 PT |
| 4,399,820 | 8/1983 | Writzfeld et al. | 128/419 PG |
| 4,566,456 | 1/1986 | Koning et al. | 128/419 PG |
| 4,567,892 | 2/1986 | Plicchi et al. | 128/419 PG |
| 4,594,565 | 6/1986 | Barreras | 128/419 PG |
| 4,596,251 | 6/1986 | Plicchi et al. | 128/419 PG |
| 4,697,591 | 10/1987 | Lekholm et al. | 128/419 PG |

FOREIGN PATENT DOCUMENTS

| 0089014 | 7/1982 | European Pat. Off. | 128/419 P |
| 0135911 | 1/1983 | European Pat. Off. | . |
| 0074126 | 6/1986 | European Pat. Off. | . |

OTHER PUBLICATIONS

"An Electroplethysmograph for Investigation Regional Lung Function," Mazhhbich et al., Biomedical Engineering, vol. 9, No. 3, pp. 177–180 (May–Jun. 1975).

Primary Examiner—Francis J. Jaworski
Attorney, Agent, or Firm—Hill, Van Santen, Steadman & Simpson

[57] ABSTRACT

A cardiac pacer which generates pacing pulses at a predetermined pacing rate, includes a device for generating an alternating signal which is unable to pace the heart. The pacing pulses and the alternating signal are transmitted together to the heart. The alternating signal after transmittal to the heart is measured and processed such that a respiratory signal is obtained. The predetermined pacing rate is then varied dependent on the respiratory signal.

18 Claims, 1 Drawing Sheet

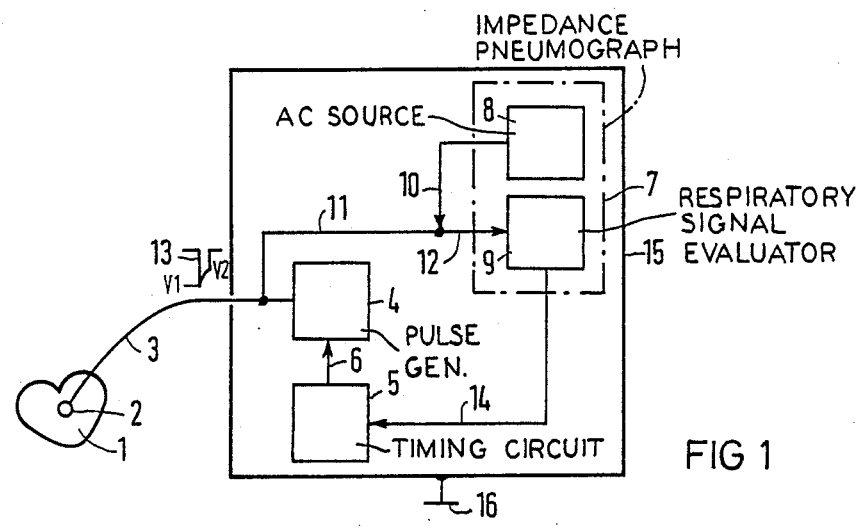
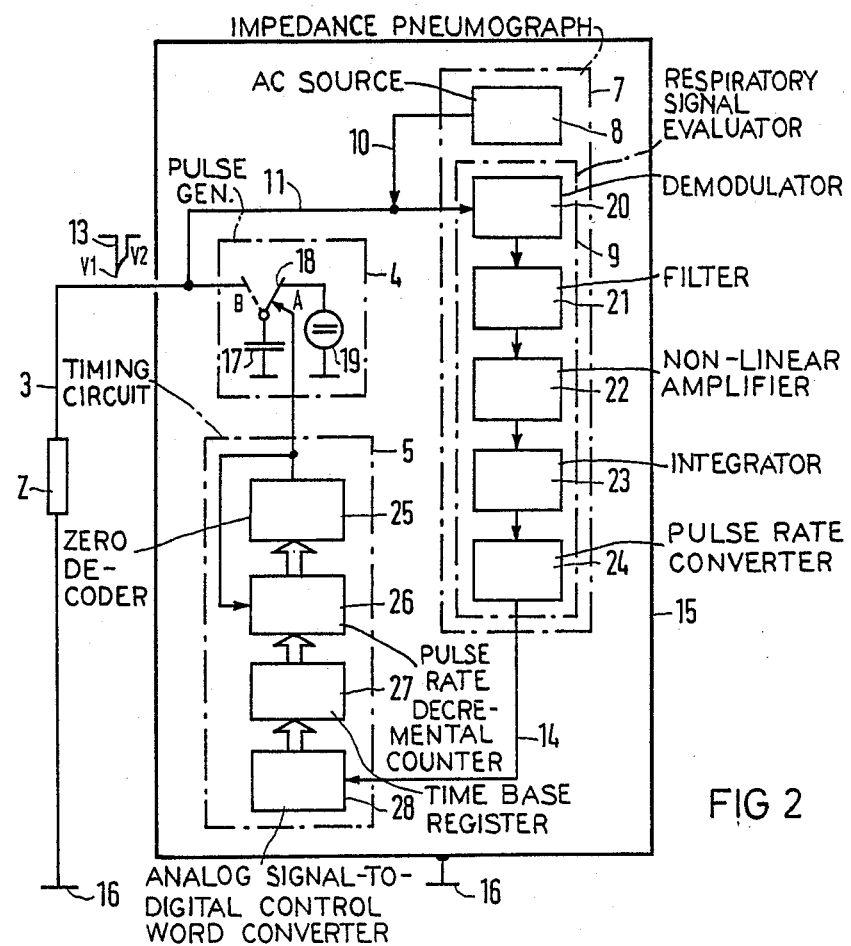

CARDIAC PACER FOR PACING A HUMAN HEART

BACKGROUND OF THE INVENTION

1. Field of the Invention

This invention relates to a cardiac pacer for pacing a human heart, wherein the pacing rate is controlled by the respiration of the patient.

2. Related Applications

The present application is related to the following applications filed simultaneously herewith: "A Cardiac Pacer For Pacing A Human Heart," Amundson, Ser. No. 874,588; "A Cardiac Pacer For Pacing A Heart," Lekholm and Amundson, Ser. No. 874,585; "A Cardiac Pacer for Pacing A Human Heart," Lekholm and Amundson, Ser. No. 874,591; and "A Cardiac Pacer For Pacing A Heart," Lekholm and Amundson, Ser. No. 874,596.

3. Description of the Prior Art

Conventional cardiac pacers usually comprise a pacing electrode and a passive electrode. The pacing electrode is placed in the human heart by means of a pacing lead. The metallic housing of the cardiac pacer defines the passive electrode.

The U.S. Pat. No. 3,593,718 describes such a conventional cardiac pacer which in addition utilizes an impedance pneumograph for obtaining a respiratory signal from thoracic impedance variations. The impedance pneumograph comprises first and second impedance measuring electrodes each connected with separate first and second leads, respectively. Both impedance measuring electrodes of the impedance pneumograph are placed on the surface of the patient's chest.

The European Patent Application No. 0 089 014 depicts a conventional cardiac pacer which also employs an impedance pneumograph for obtaining a respiratory signal. Again the impedance pneumograph comprises first and second impedance measuring electrodes. However, only the first impedance measuring electrode is connected to a lead while the second electrode is defined by the conductive (metallic) housing which contains the cardiac pacer and the impedance pneumograph. Furthermore, the first impedance measuring electrode and, because the conductive (metallic) housing is implanted, also the second electrode, are subcutaneously placed in the thorax. Under the circumstances the complete pacing and impedance measuring system comprises a pacing electrode on a first lead, a first impedance measuring electrode on a second lead and the metallic housing as both the passive electrode of the cardiac pacer and the second electrode of the impedance pneumograph.

SUMMARY OF THE INVENTION

1. Objects

It is an object of this invention to provide a cardiac pacer for pacing a human heart wherein the pacing rate is controlled by the respiration rate of the patient and wherein the number of necessary electrodes and therefore also the number of necessary leads for obtaining a respiratory signal from thoracic impedance variations is reduced to a minimum.

2. Summary

According to this invention an improved cardiac pacer for pacing a human heart is provided which comprises (a) means for generating pacing pulses at a predetermined pacing rate;
(b) means for generating an alternating signal which is unable to pace the heart;
(c) means for transmitting the pacing pulses together with the alternating signal to the heart;
(d) means for measuring and processing the alternating signal after transmittal to heart for obtaining a respiratory signal; and
(e) means for varying the predetermined pacing rate dependent on the respiratory signal.

The invention operates with only two electrodes and one lead for both pacing and measuring the impedance variations, namely the pacing electrode connected to the pacing lead and the conductive (metallic) housing containing the pacer and the impedance pneumograph. Under the circumstances the invention provides for a minimum number of electrodes and leads for pacing and impedance measurement.

In a preferred embodiment of the invention the alternating signal generating means are designated for generating an alternating current having an amplitude, the amplitude being dependent on the frequency of the alternating signal and lying substantially below the fibrillation threshold of the heart (e. g. $<10\ \mu A$, preferably at $2\ \mu A$). The frequency lies above 150 Hz, e. g. in the range of 1 kHz to 10 kHz, preferably at 4 kHz.

The foregoing and other objects, features and advantages of the invention will be apparent from the following more particular description of a preferred embodiment of the invention, as illustrated in the accompanying drawings.

BRIEF DESCRIPTION OF THE DRAWINGS

FIG. 1 shows the invention in a schematic flock diagram; and

FIG. 2 illustrates the invention in a more detailed block diagram.

DESCRIPTION OF THE PREFERRED EMBODIMENT

In FIG. 1 a human heart which has to be paced is generally designated with 1. A pacing electrode 2 is inserted in the human heart 1 in a manner and position that the heart can most efficiently be paced. The pacing electrode 2 is connected through a pacing lead 3 with a pacing pulse generator 4. A timing circuit 5 controls the pacing rate of the pacing pulse generator 4 through line 6.

An impedance pneumograph (also called a pneumatograph) 7 comprises an AC source 8 generating a continuous or a duty cycled (e.g. by the heart cycle or a clock) alternating current, and a device 9 for measuring and evaluating a respiratory signal from the continuous alternating current after transmittal to the heart. The AC source 8 is connected with the pacing lead 3 through leads 10, 11. The device 9 is connected with the pacing lead 3 through leads 11, 12. Under the circumstances the current of the AC source 8 is supplied to the pacing electrode 2 together with the pacing pulses 13 according to this invention.

The impedance pneumograph 7 controls the timing circuit 5 through line 14 in a manner that a predetermined basic pacing rate of the pacing pulse generator 4 is varied dependent on the respiratory signal.

In FIG. 1 the pacing pulse generator 4, the timing circuit 5 and the impedance pneumograph 7 are all encapsuled in an implantable conductive (metallic)

housing 15 which is the housing of the cardiac pacer according this invention. The conductive (metallic) housing 15 defines both the passive electrode for pacing and the second electrode for impedance measurement as indicated in FIG. 1 with reference numeral 16. Under the circumstances the cardiac pacer according to this invention operates with only two electrodes and one lead, namely electrodes 2 and 16 and lead 3 for both pacing and impedance measurement.

FIG. 2 depicts the schematic block diagram of FIG. 1 in more detail. The complete impedance including the heart is generally designated with Z. The pacing pulse generator 4 comprises an output capacitor 17 which is switchable by means of switch 18 between battery 19 (switch position A) and pacing lead 3 (switch position B). In switch position A the output capacitor 17 is charged by the battery 19 to a voltage V1. In switch position B the output capacitor 17 is discharged through pacing lead 3 as pacing pulse 13.

The device 9 comprises a demodulator 20 for the alternating current picked up from the patient, a filter 21, a non-linear amplification (e.g. squaring) circuitry 22, an integrator 23 and a voltage to pulse rate converter 24. The non-linear amplification circuitry 22 amplifies the output signal of filter 21 such that signal portions having higher amplitudes are more amplified than signal portions having lower amplitudes. Under the circumstances signal portions of interest including the respiration signal are enhanced with respect to low amplitude noise for further processing. Non-linear amplification circuits of this kind are well known in the art and need not be described in more detail. The output signal of the non-linear amplification circuitry 22 is integrated in integrator 23 over a period of time, e. g. in the range of 5 to 30 s. By integrating, high-frequency noise is significantly reduced. The voltage to pulse rate converter 24 converts the integrated signal into a pulse rate according to the breathing rate.

The timing circuit 5 comprises a zero decoder 25, a pulse rate down counter 26, a time base register 27 and an analog signal to digital control word converter 28. The converter 28 converts the pulse rate signal of the voltage to pulse rate converter 24 into a digital control word. This digital control word is supplied to the time base register 27. It controls the time base register 27 such that a basic pacing rate, e.g. 60 beats/min., is varied dependent on the respiration rate. When the breathing rate increases the time base register 27 increases the counting speed of decremental counter 26 so that it reaches zero faster than at the basic rate. Under these conditions the zero decoder 25 generates switching signals at higher rates, so that the output capacitor 17 of the pacing pulse generator 4 charges and discharges at higher rates. As a result the pacing rate increases dependent on increasing breathing rate as desired.

Having thus described the invention with particular reference to the preferred forms thereof, it will be obvious to those skilled in the art to which the invention pertains, after understanding the invention, that various changes and modifications may be made therein without departing from the spirit and scope of the invention as defined by the claims appended hereto.

What is claimed is:

1. A cardiac pacer for pacing a human heart in a patient comprising
    (a) means for generating pacing pulses at a predetermined pacing rate;
    (b) means for generating an alternating signal having an amplitude less than that necessary to pace the heart;
    (c) means connected to said means for generating pacing pulses and to said means for generating an alternating signal for transmitting the pacing pulses together with the alternating signal directly to the heart along a common transmission path wherein said alternating signal is modified at least in part by the respiratory activity of said patient, and for receiving said modified alternating signal from said heart,
    (d) means connected to said means for transmitting and receiving for processing the alternating signal after transmittal to the heart for obtaining a respiratory signal therefrom; and
    (e) means for varying the predetermined pacing rate dependent on the respiratory signal.

2. A cardiac pacer as claimed in claim 1, wherein said alternating signal generating means generates an alternating current having an amplitude, said amplitude being dependent on the frequency of said alternating signal lying substantially below the fibrillation threshold of the heart.

3. A cardiac pacer as claimed in claim 2, wherein said alternating signal generating means generates an alternating current having an amplitude, said amplitude being dependent on the frequency of said alternating signal and lying substantially below the fibrillation threshold of the heart at frequencies above 150 Hz.

4. A cardiac pacer as claimed in claim 3, wherein said alternating signal generating means generates an alternating current in the frequency range of 1 kHz to 10 kHz.

5. A cardiac pacer as claimed in claim 4, wherein said frequency is 4 kHz.

6. A cardiac pacer as claimed in claim 4, wherein said alternating signal generating means generates an alternating current having an amplitude which is smaller than 10 $\mu$A.

7. A cardiac pacer as claimed in claim 5, wherein said alternating current is smaller than 2 $\mu$A.

8. A cardiac pacer as claimed in claim 1, wherein said means for processing the alternating signal includes a demodulator for the alternating signal received from said heart.

9. A cardiac pacer as claimed in claim 1, wherein said means for processing the alternating signal includes means for non-linearly amplifying the respiratory signal such that signal portions having higher amplitudes are more amplified than signal portions having lower amplitudes, means for integrating the non-linearly amplified respiratory signal over a period of time, and wherein said means for varying the predetermined pacing rate varies said pacing rate dependent on the integrated signal.

10. A cardiac pacer as claimed in claim 9, wherein said period of time is in the range 11. A cardiac pacer as claimed in claim 1, wherein said means for processing the alternating signal further includes a voltage to pulse rate converter for the integrated signal connected to an output of said means for integrating.

12. A cardiac pacer as claimed in claim 11, wherein said means for varying the predetermined pacing rate comprises an analog signal to digital control word converter for the output signal of the voltage to pulse rate converter, a time base register for the output signal of the analog signal to digital control word converter, a decremental counter for the output signal of said time base register which is set to higher zero counting speed as the respiration rate increases, and a zero decoder at the output of the decremental counter, said zero decoder being connected with and controlling the pacing pulse generator such that a pacing pulse is generated at each zero count.

13. A cardiac pacer as claimed in claim 1, wherein said alternating signal generating means is a means for generating a continuous alternating signal.

14. A cardiac pacer as claimed in claim 1, wherein said alternating signal generating means is a means for generating a duty cycled alternating signal.

15. A cardiac pacer as claimed in claim 14, wherein the means for generating a duty cycled alternating signal includes means for duty cycling the alternating signal on the cardiac cycle or clock.

16. A cardiac pacer as claimed in claim 1, wherein said cardiac pacer further comprises a metallic housing forming a passive electrode, and wherein said means for transmitting and receiving includes a single lead terminating in a single active electrode.

17. A cardiac pacer for pacing a heart in a patient comprising:
  means for generating pacing pulses at a selecting pacing rate;
  means for generating an additional non-constant signal having an amplitude less than that necessary to pace said heart;
  means for transmitting said pacing pulses and said additional signal directly to said heart via a single active electrode, said additional signal being altered at least in part by respiratory activity of said patient, and for receiving the altered signal via said single active electrode;
  means for processing said altered signal for obtaining a respirator signal therefrom; and
  means for varying said selected pacing rate in dependence upon said respiratory signal.

18. A method for pacing a heart in a patient comprising:
  generating pacing pulses at a selected pacing rate;
  generating an additional non-constant signal having an amplitude less than that necessary to pace said heart;
  simultaneously transmitting said pacing pulses and said additional signal to said heart via a single active electrode, said additional signal being altered at least in part by respiratory activity of said patient;
  receiving the altered signal from said heart via said single active electrode;
  processing said altered signal for obtaining a respiratory signal therefrom; and
  varying said selected pacing rate in dependents on said respiratory signal.

* * * * *